United States Patent [19]
Walker et al.

[11] Patent Number: 6,050,967
[45] Date of Patent: Apr. 18, 2000

[54] BANDAGE COMPRESSION INDICATOR

[75] Inventors: Marshall H. Walker, Johnson County; Fred M. Trainor; George P. Hansen, both of Tarrant County, all of Tex.

[73] Assignees: Avcor Health Care Products, Inc., Fort Worth; Johnson & Johnson Medical, Inc., Arlington, both of Tex.

[21] Appl. No.: 09/192,918

[22] Filed: Nov. 16, 1998

Related U.S. Application Data

[63] Continuation of application No. 08/853,090, May 8, 1997, abandoned.

[51] Int. Cl.[7] ........................................... A61F 5/00
[52] U.S. Cl. ................................. 602/75; 602/76
[58] Field of Search ............................... 73/760; 602/19, 602/53, 75, 76, 77, 78

[56] References Cited

U.S. PATENT DOCUMENTS

| | | | |
|---|---|---|---|
| 3,613,679 | 10/1971 | Bijou | 602/75 |
| 4,286,603 | 9/1981 | Marshall | 600/595 |
| 4,421,124 | 12/1983 | Marshall | 600/491 |
| 4,437,408 | 3/1984 | Arkans | 101/483 |
| 4,665,909 | 5/1987 | Trainor | 602/75 |
| 5,195,950 | 3/1993 | Delannoy | 602/72 |
| 5,503,620 | 4/1996 | Danzger | 602/19 |
| 5,779,659 | 7/1998 | Allen | 602/75 |

*Primary Examiner*—Richard J. Apley
*Assistant Examiner*—Kim M. Lee
*Attorney, Agent, or Firm*—Jack A. Kanz

[57] ABSTRACT

Visual indication of compressive force applied by a compression bandage is provided by forming a continuous pattern of repeated geometric shapes in the bandage strip with indicator yarn. The continuous pattern is formed so that the shape of each geometric design is changed when tension is applied to the bandage and the shape of the deformed pattern is indicative of compression force applied.

10 Claims, 3 Drawing Sheets

BANDAGE COMPRESSION INDICATOR

This is a continuation of application Ser. No. 08/853,090 filed May 8, 1997 entitled Bandage Compression Indicator, now abandoned.

This invention relates to compression bandages. More particularly, it relates to indicators integrally formed in compression bandages which form a continuous graphic display indicative of the compressive force exerted by the bandage when stretched and applied.

Various pathological conditions and therapeutic treatments require application of compressive force to human body parts. Typically, the required compressive force is applied by wrapping an elongated elastic bandage around a body part such as a leg, arm, etc., under sufficient tension so that the multi-layered wrapping of bandage applies uniform compression to the body part. While the tension applied to a stretched bandage is proportional to the compressive force applied by the bandage, it is difficult to accurately determine the amount of compressive force without accurate means for measuring tension. Simply wrapping the bandage and attempting to judge tension by feel is far too inaccurate and imprecise in most cases.

Various visual indicators have been devised to measure the elongation of compression bandages and thereby indicate the resulting pressure applied. For example, U.S. Pat. No. 3,613,679 discloses a compression bandage having marks of variable geometric form distributed over the length thereof. The degree of elongation of the bandage (and, consequently, the resulting pressure applied) is visually indicated by deformation of the marks. Similarly, France Patent No. 2,544,982 discloses rows of parallel dots spaced and arranged so that stretching of the bandage re-arranges the dots in a manner which indicates the amount of stretch (and therefore the compressive force) applied.

All conventional tension or compressive force indicators, however, suffer from one or more of various deficiencies. For example, most such indicators are applied to the bandage fabric after manufacture of the bandage by applying a dye or other marker to the fabric. Since such markers must be applied to the fabric while the fabric is stretched, accurate means for measuring applied tension must be used in conjunction with precise marking apparatus. No commercially practical apparatus for performing this task has yet been devised. Furthermore, markers and the like applied to the surface of a knit or woven bandage are not sharply defined and tend to fade with use. Such deficiencies render the compression indicators conventionally in use less than adequate and/or insufficient in other ways.

In accordance with the present invention, an indicator is integrally formed in the bandage as it is formed by including within the fabric structure an indicator yarn of color which visibly contrasts with the apparent color of the bandage. The indicator yarn is formed into a continuous pattern of repeated geometric shapes which change shape when the bandage is stretched. In the preferred embodiment, two indicator yarns are laid in the front face of a knitted strip during knitting. The indicator yarns are colored to contrast with the visually perceived color of the bandage strip and inserted parallel with each other and parallel with the wales (longitudinally) of the knitted strip. At predetermined intervals along the length of the indicator yarn, each indicator yarn is deviated toward the other indicator yarn to form a deviated portion (excursion) of the indicator yarn which lies substantially parallel with the weft (perpendicular to the wales). Thus, the parallel base lines of the indicator yarns define a continuous strip or track interconnected by perpendicular excursions which define rectangles in the face of the knit strip. By proper placement and orientation of the excursions and the parallel base lines, the rectangles may be stretched to form a string of squares when a predetermined tension is applied to the bandage strip. Since tension is directly related to compressive force applied; and since the indicator yarn is physically constrained within the knit fabric, distortion of the fabric by stretching can be directly translated to compressive force and accurately determined by distortion of the indicator yarn. Thus, the indicator yarn provides an accurate, precise and durable indication of compressive force.

Other advantages of the invention will become more readily understood from the following detailed description taken in connection with the appended claims and attached drawing in which:

Throughout the several views of the drawing like numerals are used to indicate like parts. The drawing views are not to scale but are intended to disclose the inventive concepts by relative illustration.

Figure 1:
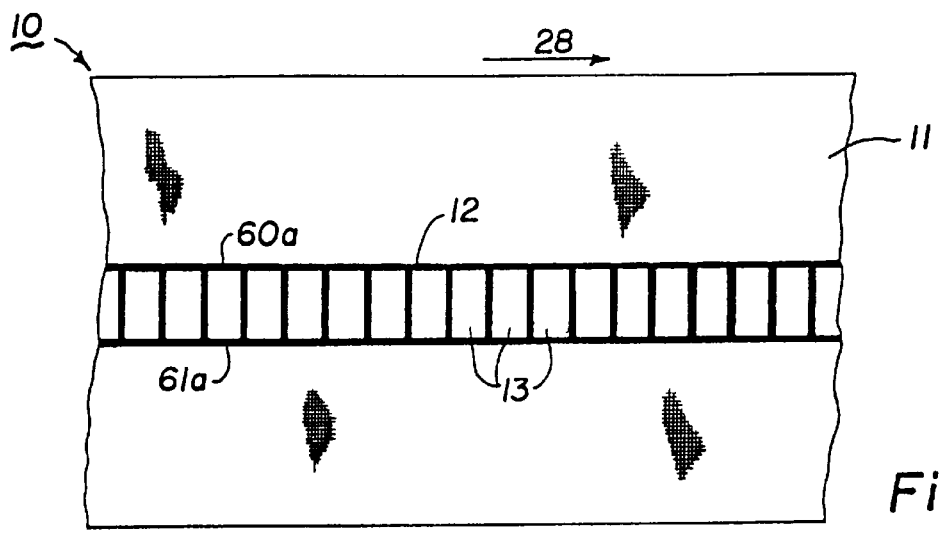
FIG. 1 is a top plan view of a segment of elastic bandage with a compression indicator formed therein in accordance with the invention.

FIG. 1 illustrates a segment 10 of knitted elastic bandage 11. The elastic bandage 11 may be any of various commercially available knit or woven materials formed on various lengths, widths, densities, etc., for use as compression bandages or windings. A typical knit bandage and method of making same is disclosed in U.S. Pat. No. 4,665,909 which was issued May 19, 1987 to Fred M. Trainor.

Figure 2:
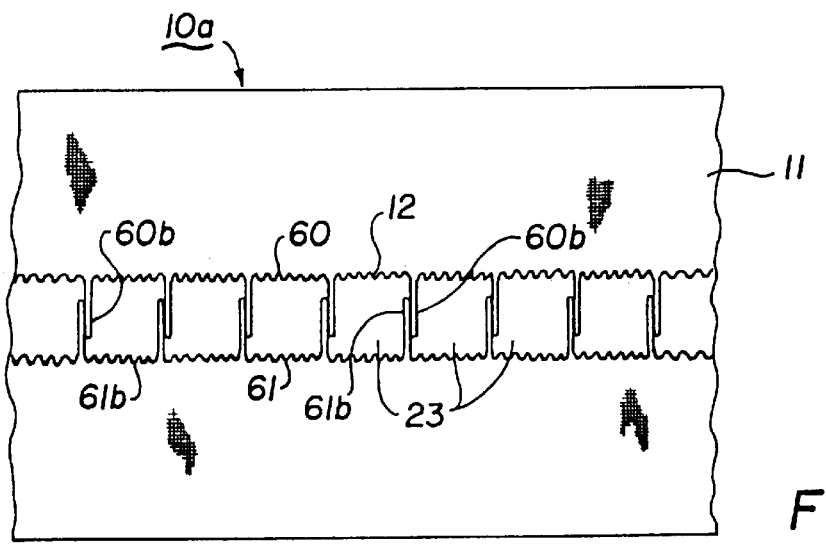
FIG. 2 is a top plan view of a shorter segment of the compression bandage of FIG. 1 stretched to exhibit an indicated compression force in accordance with the invention.

As shown in FIG. 1, the indicator yarn is positioned within the elastic bandage 11 to define a continuous pattern 12 comprised of adjoining rectangles 13 extending the length of the strip. The yarn which forms the continuous pattern 12 is contained within the elastic bandage in two parallel rows, each of which parallels the wales of the strip. At predetermined spaced intervals each of the indicator yarns 60, 61 is deviated toward the other (as more clearly illustrated in FIGS. 2 and 3) so that the opposed excursions merge to define parallel interconnection bars 60b, 61b between the parallel yarn base lines. The parallel bars, in cooperation with the parallel yarn base lines, define a series of rectangles 13.

Figure 3:
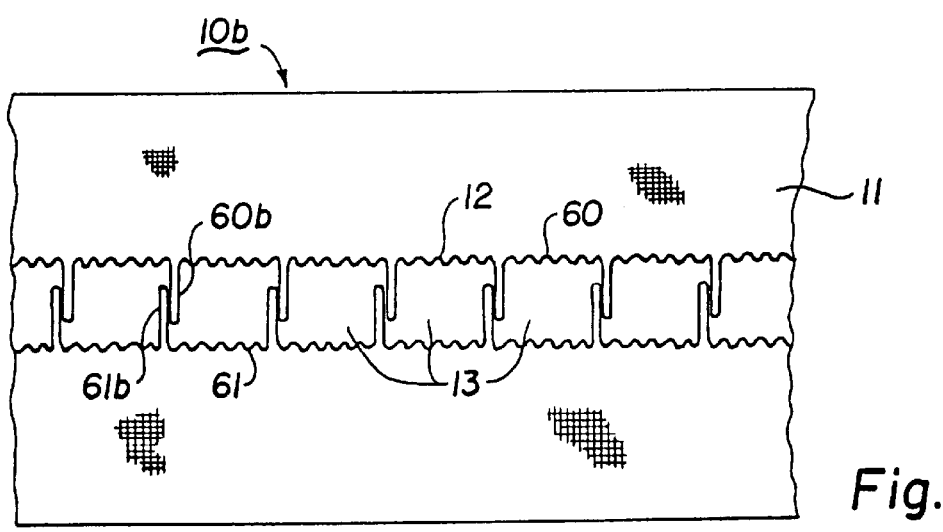
FIG. 3 is a top plan view of a shorter segment of the compression bandage of FIG. 2 stretched to illustrate the appearance of the indicator of the invention in an overstretched condition.

It will be appreciated that the knitted strip is formed in the stretched condition. Thus, the indicator yarn is positioned parallel with the wales of the knit in its fully extended condition. However, as the elastic bandage contracts, the indicator yarn is compressed axially to form rather enlarged indicator pattern lines 60a, 61a as shown in FIG. 1. As shown in FIG. 3, the indicator yarn 60, 61 in each row deviates inwardly toward the other row and may overlap as shown. When the bandage is stretched, the overlap of the yarn forming an indicator bar may become visually apparent.

Figure 4:
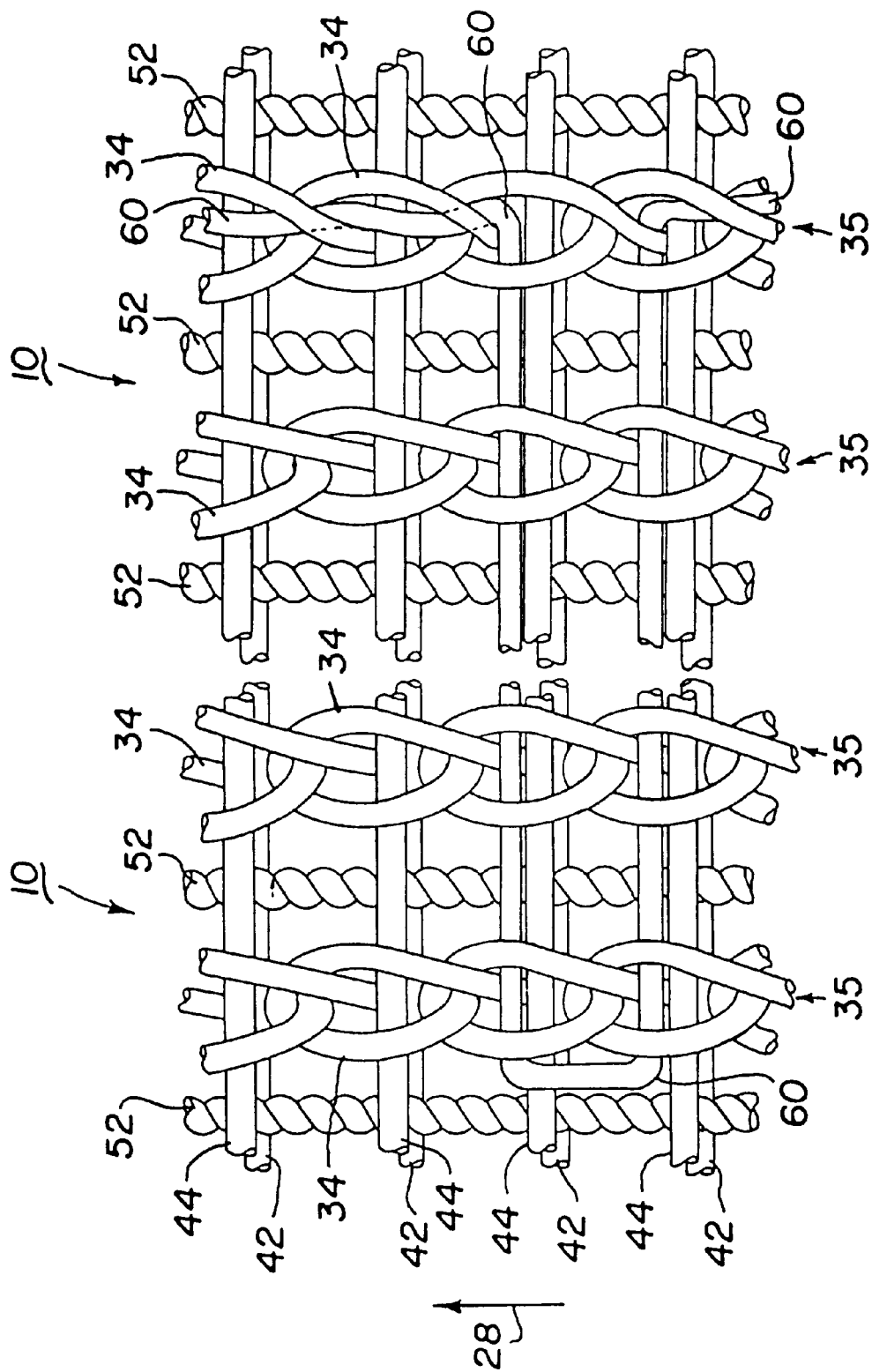
FIG. 4 is a fragmentary pictorial view of a segment of knitted compression bandage illustrating placement of the indicator yarn therein.

Inclusion of an indicator yarn in a knitted strip is disclosed in detail in FIG. 4 which illustrates formation of a knit yarn as disclosed in Trainor 4,665,909, supra, which is incorporated herein by reference. As shown in FIG. 4, the segment 10 is formed with a plurality of knitted warp yarns 34 forming individual, unconnected wales or columns 35 extending the full length of the fabric strip parallel with each other in direction 28. Front and back strands of weft or filling yarn 44 and 42, respectively, are interwoven or floated within the knitted wales of the warp yarns in transverse direction between each side edge of the fabric to define a plurality of aligned front and back courses. Each pick or course of front and back weft yarn passes through and engages each loop of warp yarn aligned with that course of fabric. A plurality of secondary warp strands 52 are longitudinally interlayed or folded between the front and back courses of the weft yarn and between and parallel with each of the wales of the primary warp yarn. The front courses of the weft yarn are thus spaced from the back courses of the weft yarn by the thickness of the secondary warp strands 52. The secondary warp yarn 52 is elastic and may be rubber or synthetic material. The secondary warp strands enable the fabric to be stretched and to exert compressive force when wrapped around a body part or the like.

In accordance with the preferred embodiment of the invention, indicator yarn 60, 61 (only yarn 60 is shown in FIG. 4) are laid within the front face of the knit fabric parallel with one column. Preferably, each indicator yarn 60, 61 is included in one column of knitted warp as shown in FIG. 4.

As illustrated in FIG. 4 a colored yarn 60 is included in the column 35 of warp 34 and thus extends parallel with longitudinal direction 28. However, at preselected spaced intervals the indicator yarn 60 deviates laterally across the wales 35 a predetermined excursion distance (parallel with weft yarn 44) and then, within a single stitch, returns to the original column. Each excursion forms a parallel deviation or interconnection bar 60b, 61b as shown in the stretched segments 10a of FIG. 2 and 10b of FIG. 3. In the preferred embodiment the excursions 60b, 61b are formed in adjacent stitches so that they may overlap and thus form a continuous deviation or indicator bar. As noted above, the indicator yarn is inserted while the knit fabric is being formed in the stretched condition. Thus, when the knitted fabric contracts, the adjacent deviation bars 60b, 61b collapse longitudinally to form a pattern visually perceived as a single enlarged bar.

In the preferred embodiment, a single strand of yarn is used as the indicator yarn in each base line 60a, 60b. However, multiple strands may be used if desired. the indicator yarn 60, 61 is merely used to form a visual marker. Thus, the term "colored" as used herein merely indicates that the visually perceived color of the indicator yarn 60, 61 is sufficiently contrasted with the visually perceived color of the knit fabric yarn so that the user may identify the pattern formed thereby.

It will be readily appreciated that although the preferred embodiment has been described with reference to two parallel strands of indicator yarn, each of which deviates toward the other to form an interconnected series of parallelograms, various other geometric designs can be formed. Likewise, both strands need not deviate toward the other. Instead, only one strand may deviate toward the other strand or vice versa. However, the use of parallel strands forming parallelograms may be performed on commercial knitting machines quite economically. The indicator yarn is used to form a continuous design so that the knitting process need not be interrupted and the indicator can be formed continuously throughout the formation process. Discontinuous or interrupted patterns cannot be formed without cutting the indicator yarn.

Various bandages have been constructed in accordance with the invention to produce compression bandages of known compressive force. In the preferred embodiment, the indicator yarn is formed to produce a continuous design of rectangles which, when stretched to present the desired compressive force, form squares. This pattern is easily recognizable by the user and thus may be properly used to apply compression bandages without further training.

Compression bandages are typically designed to produce a specified compression (measure in mm Hg) when stretched approximately 50%. This is commonly referred to as 50% compression. The actual compressive force is determined by the geometry of the body wrapped. Thus, the bandage is usually designed to produce a specified compressive force on a specified object. The principles of the invention have been used to form a four (4) inch wide 50% compression bandage which produces 40 mm Hg compression at the ankle portion of a human leg with the following:

2 strands nylon (70/2)

28 strands polyester (1/150 d.)

27 strands polypropylene (210 d.)

4 strands cotton (30/1)

56 strands rubber (60 ga.)

An additional two (2) strands of blue polyester (150 d.) were used to form the indicator. The parallel indicator strands 60, 61 were inserted ⅝ inch apart to form parallel tracks on either side of the centerline with interconnection bars 60b, 61b spaced ⅝ inch apart (inside dimensions) at 50% compression. Since this fabric was knitted at 210% stretch, the deviations were spaced a proportional distance apart during fabrication, thus forming rectangles elongated in the longitudinal direction when formed. However, in the relaxed condition the indicator yarns are compressed and the squares become rectangles elongated in the transverse direction. Nevertheless, when the bandage strip is stretched to 50% compression, each rectangular design becomes a ⅝ inch by ⅝ inch square.

A similar four (4) inch wide 50% compression bandage was made with:

2 strands nylon (70/2)

36 strands polyester (1/150 d.)

18 strands polypropylene (210 d.)

2 strands cotton (36/1)

56 strands rubber (90 ga.)

An additional two (2) strands of colored polyester (150 d.) were inserted as described above in parallel warps on either side of the centerline and separated by a distance of ¾ inch. The bandage was knitted at 180% stretch and the deviations (interconnection bars 60b, 61b) were spaced to be ¾ inch apart (inside dimensions) at 50% compression. This strip also executed a compression force of 40 mm Hg on the human leg at the ankle when the indicator design was stretched to produce a repetitive series of ¾ inch×¾ inch squares.

The foregoing examples merely illustrate variations in construction which may be used to exploit the principles of the invention. The strips of the examples were made in four (4) inch widths merely for convenience. Compression bandages can be made in any length or width desired and designed to exert a specified compressive force at any degree of stretch desired. The principles of the invention are equally applicable to all such variations in bandage design.

Figure 5:
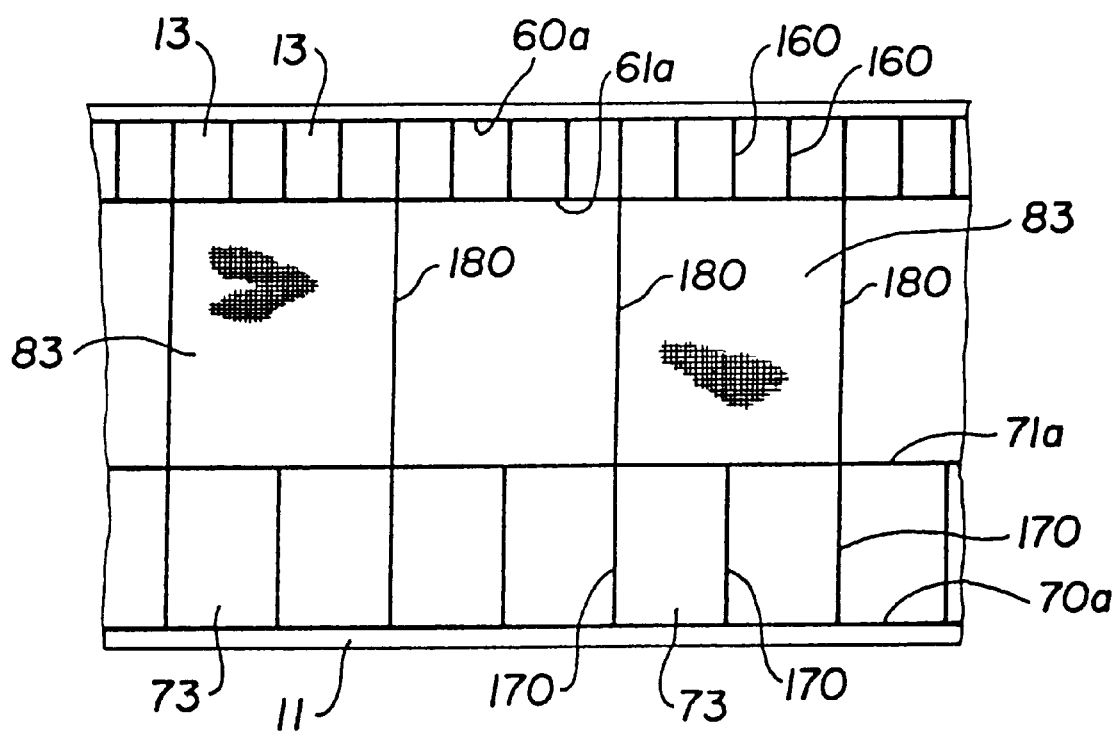
FIG. 5 is a top plan view of a segment of elastic bandage with an alternative embodiment of the compression indicator of the invention formed therein.

FIG. 5 illustrates an embodiment of the invention wherein three (3) different degrees of stretch (and therefore values of compressive force) may be readily determined visually. In this case, four (4) parallel base lines 60a, 61a, 70a, 71a are used to define three (3) sets of indicator figures. Parallel base lines 60a, 61a interconnected by indicator bars 160 are formed as described above. This series of figures (adjacent rectangles as shown) is positioned off center as shown. A second set of parallel base lines 70a, 71a interconnected by indicator bars 170 is positioned off center on the opposite side of the top face of the bandage. Parallel base lines 61a and 71a are interconnected by a third set of indicator bars 180. By appropriately placing the base lines 60a, 61a, 70a, 71a with respect to each other, indicator bars 160, 170, 180 may be formed to define three (3) sets of interconnected rectangles 13, 73, 83, each of which will be stretched to form a series of interconnected squares under different degrees of tension. Thus bandage 11 may be applied to indicate a first stretch when the rectangles 13 become squares; a second (greater) stretch when the rectangles 73 become squares; and a third (even greater) stretch when the rectangles 83 become squares.

While the invention has been described with particular reference to forming indicator patterns which deform to produce square figures when the proper tension is applied to knitted bandages, the invention is not so limited. Various other continuous (open or closed) designs which deform to readily recognizable stretched designs (such as interconnectioned diamonds or other parallelograms) may also be used and the principles of the invention are equally applicable to woven fabrics. Furthermore, two parallel indicator yarns are not necessarily required. For example, a single yarn with lateral excursions at selected intervals could be used to form open figure patterns. As indicated above, the indicator pattern need not be placed at the geometric center of the bandage. Nor is the invention limited to use of a single band of indicator. The indicator may be formed, for example, adjacent one edge or, if preferred, adjacent both edges. it is to be understood, therefore, that although the invention has been described with particular reference to specific embodiments thereof, the forms of the invention shown and described in detail are to be taken as preferred embodiments same. Various changes and modifications may be resorted to without departing from the spirit and scope of the invention as defined by the appended claims.

What is claimed:

1. An elastic fabric compression bandage comprising an indicator yarn disposed therein to form a continuous pattern of repeated geometric shapes extending throughout its length, said continuous pattern of repeated geometric shapes changes shape when the bandage is stretched to indicate a predetermined tension applied to the bandage wherein said indicator yarn defines in an unstretched condition two continuous base lines extending parallel with each other in a longitudinal direction with at least one baseline having a periodic excursion in a direction perpendicular to the other baseline to define a repetitive series of geometric shapes.

2. A bandage as defined in claim 1 wherein said indicator yarn defines a pattern of adjacent substantially rectangular figures which are transformed into adjacent substantially square figures when a predetermined tension is applied to the bandage.

3. A bandage as defined in claim 1 wherein said indicator yarn defines at least three continuous base lines extending parallel with each other in the longitudinal direction.

4. A bandage as defined in claim 1 wherein each baseline has a periodic excursion toward the other baseline and wherein said periodic excursions overlap.

5. A bandage as defined in claim 1 wherein said indicator yarn is comprised of a plurality of individual strands of material.

6. A bandage as defined in claim 1 wherein said indicator yarn defines a pattern including at least two parallel rows of adjacent substantially rectangular figures and wherein each of said rows of adjacent substantially rectangular figures is transformed into a row of adjacent substantially square figures when predetermined tensions are applied to the bandage.

7. A bandage as defined in claim 1 wherein said bandage is an elongated strip of knitted fabric.

8. An elastic fabric bandage strip including a yarn therein in two continuous parallel lines which define opposing parallel base lines of a continuous pattern of first geometric shapes on at least one face of said strip when the elastic fabric bandage is in the relaxed condition and a continuous pattern of second geometric shapes indicative of a predetermined amount of tension applied to said strip when said strip is stretched in a longitudinal.

9. A bandage as defined in claim 8 wherein said pattern of first geometric shapes is a continuous pattern of adjacent rectangles elongated transversely to the longitudinal direction of said strip and said pattern of second geometric shapes is a continuous pattern of adjoining squares.

10. A method of marking elastic bandages to indicate the tension applied thereto comprising:

(a) forming an elastic bandage strip which is longitudinally elongatable; and (b) inserting into said bandage strip during formation thereof an indicator yarn arranged to define in an unstretched condition two continuous parallel base lines interconnected by excursions from at least one of said parallel base lines to display on at least one face of said bandage strip a continuous pattern of first geometric figures when said strip is in a relaxed unstretched condition which is transformed into a continuous pattern of second geometric figures indicative of a predetermined amount of tension applied to said strip when said strip is elongated by stretching.

\* \* \* \* \*

UNITED STATES PATENT AND TRADEMARK OFFICE
CERTIFICATE OF CORRECTION

PATENT NO. : 6,050,967
DATED : April 18, 2000
INVENTOR(S) : Marshall H. Walker, et. al.

It is certified that error appears in the above-indentified patent and that said Letters Patent is hereby corrected as shown below:

Column 6, line 33, "longitudinal." should read --longitudinal direction--

Signed and Sealed this

Sixth Day of March, 2001

Attest:

NICHOLAS P. GODICI

Attesting Officer    Acting Director of the United States Patent and Trademark Office